US007494807B2

(12) United States Patent
Nakorn et al.

(10) Patent No.: US 7,494,807 B2
(45) Date of Patent: Feb. 24, 2009

(54) MAMMALIAN MEGAKARYOCYTE PROGENITOR CELL

(75) Inventors: Thanyaphong Na Nakorn, Stanford, CA (US); Toshihiro Miyamoto, Fukuoka (JP); Irving L. Weissman, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 156 days.

(21) Appl. No.: 10/661,455

(22) Filed: Sep. 12, 2003

(65) Prior Publication Data
US 2005/0176142 A1 Aug. 11, 2005

Related U.S. Application Data

(60) Provisional application No. 60/410,490, filed on Sep. 13, 2002.

(51) Int. Cl.
*C12N 5/00* (2006.01)
(52) U.S. Cl. ..................... 435/325; 424/93.7
(58) Field of Classification Search ............... None
See application file for complete search history.

(56) References Cited

U.S. PATENT DOCUMENTS

| 6,465,247 B1 | 10/2002 | Weissman et al. |
| 2002/0086422 A1 | 7/2002 | Weissman |

FOREIGN PATENT DOCUMENTS

| WO | 01/00788 | 1/2001 |

OTHER PUBLICATIONS

Clay D et al. 2001. CD9 and megakaryocyte differentiation. Blood 97: 1982-1989.*
"Methocult M3231 methylcellulose medium for mouse cells: Product Information Sheet." StemCell Technologies, Inc. Retrieved on the Internet <URL://www.stemcell.com/technical/03231-PIS.pdf>. Retrieved on Jan. 9, 2009. 3 pages.*
Akashi et al., A Clonogenic Common Myeloid Progenitor That Gives Rise To All Myeloid Lineages, *Nature*, (2000), 404, 193-197.
Burstein et al., Characteristics of Murine Megakaryocytic Colonies in vitro, *Blood*, (1979), 54, 169-179.
Enver et al., Do Stem Cells Play Dice?, *Blood*, (1998), 92, 348-351.
Georgopoulos et al., The Role of Ikaros Gene in Lymphocyte Development and Homeostasis, Annu. Rev. Immunol., (1997), 15:155-176.
Long et al., Immature Megakaryocytes in the Mouse: in Vitro Relationship to Megakaryocyte Progenitor Cells and Mature Megakaryocytes, *J. Cell. Physiol.*, (1982), 112, 339-344.
Long et al., Role of Phorbol Diesters in in Vitro Murine Megakaryocyte Colony Formation, *J. Clin. Invest.*, (1984), 74, 1686-1692.
Morrison et al., The Aging of Hematopoietic Stem Cells, *Nat Med*, (1996), 2, 1011-1016.
Morrison et al., The Long-Term Repopulating Subset of Hematopoietic Stem Cells is Deterministic and Isolatable by Phenotype, *Immunity*, (1994), 1, 661-673.
Na Nakorn et al., Myeloerythroid-Restricted Progenitors are Sufficient to Confer Radioprotection and Provide the Majority of Day 8 CFU-S, *J. Clin. Invest.*, (2002), 109, 1579-1585.
Orkin et al., Development of the Hematopoietic System, *Curr. Opin. Genet. Dev.*, (1996) 6:597-602.
Paulus et al., Polyploid Megakaryocytes Develop Randomly From a Multicompartmental System of Committed Progenitors, *Proc. Natl. Acad. Sci. USA*, (1982), 79, 4410-4414.
Singh et al., Gene Targeting Reveals a Hierarchy of Transcription Factors Regulating Specification of Lymphoid Cell Fates, Curr.Opin. Immunol., ( 1996), 8:160-165.
Spangrude et al. Purification and Characterization of Mouse Hematopoietic Stem Cells, *Science*, (1988), 241, 58-62.
Uchida et al., Rapid and Sustained Hematopoietic Recovery in Lethally Irradiated Mice Transplanted With Purified Thy-1.1$^{lo}$ LIN$^-$SCA-1$^+$ Hematopoietic Stem Cells, *Blood*, (1994), 83, 3758-3779.
Banu et al., Modulation of Haematopoietic Progenitor Development by FLT-3 Ligand, Cytokine, 1999, 11(9): 679-688.
Guerriero et al., Unilineage Megakaryocytic Proliferation and Differentiation of Purified Hematopoietic Progenitors in Serum-Free Liquid Culture, Blood, 1995, 86(10): 3725-3736.
Tao et al., Megakaryocytopoiesis: Cord Blood is Better Than Bone Marrow for Generating Megakaryocytic Progenitor Cells, Exp. Hematol., 1999, 27: 293-301.
Bartolini; et al., "Megakaryocytic progenitors can be generated ex vivo and safely administered to autologous peripheral blood progenitor cell transplant recipients", Blood, Apr. 15, 1997, 89(8):2679-88.
Hodohara; et al., "Stromal cell-derived factor-1 (SDF-1) acts together with thrombopoietin to enhance the development of megakaryocytic progenitor cells (CFU-MK)", Blood, Feb. 1, 2000, 95(3):769-75.
Manz Markus G; et al., "Prospective isolation of human clonogenic common myeloid progenitors", PNAS, Sep. 3, 2002, 99(18):11872-7.
Nakorn Thanyaphong Na; et al., "Characterization of mouse clonogenic megakaryocyte progenitors", PNAS, Jan. 7, 2003, 100(1):205-10.
Sawai N; et al., "Apoptosis of erythroid precursors under simulation with thrombopoietin: contribution to megakaryocrytic lineage choice", Stem Cells, 1999, 17(1):45-53.

* cited by examiner

*Primary Examiner*—Lora E Barnhart
(74) *Attorney, Agent, or Firm*—Bozicevic, Field & Francis LLP; Pamela J. Sherwood

(57) ABSTRACT

A substantially enriched mammalian hematopoietic cell population is provided, which is characterized as a progenitor cell committed to the megakaryocyte lineage. Methods are provided for the isolation and culture of these cells. The cell enrichment methods employ reagents that specifically recognize CD9 and CD41, in conjunction with other markers expressed on lineage committed progenitor cells. These cells give rise exclusively to megakaryocytes and platelets, as evidenced by their growth and differentiation in vitro and in vivo.

1 Claim, 4 Drawing Sheets

A

CMP 0.78% = MKP

MEP 0.33% = MKP

US 7,494,807 B2

MAMMALIAN MEGAKARYOCYTE PROGENITOR CELL

GOVERNMENT SUPPORT

This research was supported by US Public Health Service Grant #CA42551. The Government may have certain rights to this invention.

BACKGROUND OF THE INVENTION

The hematopoietic system comprises dynamic populations of blood cells, including erythrocytes, lymphocytes, monocytes, polymorphonuclear cells, e.g. basophils, eosinophils, and neutrophils; and megakaryocytes. All of these diverse cells are derived from the pluripotential hematopoietic stem cell. Through a series of cell divisions, there is a differentiation to one of these lineages. It is believed that, at least in vivo, after each cell division the developmental potential of the daughter cells is either maintained or further restricted relative to the parent, never expanded. One therefore observes that pluripotential stem cells give rise to multi-lineage committed progenitor cells, which give rise to specific lineages and finally mature cells. The coordinated changes of cellular properties leading to irreversible restriction of lineage commitment may be due to sequential activation or silencing of various genes.

Unfractionated mouse bone marrow has been shown to contain multiple types of colony-forming units (CFU), including multipotent CFU for all myeloid cells (CFU-GEMM or CFU-Mix), bipotent CFU for granulocytes and macrophages (CFU-GM), for megakaryocytes and erythrocytes (CFU-MegE), as well as monopotent CFU for granulocytes (CFU-G), macrophages (CFU-M), erythrocytes (CFU-E), or megakaryocytes (CFU-MK).

Three different populations of myeloid progenitors have been individually characterized: common myeloid progenitors (CMP), granulocyte/monocyte progenitors (GMP) and megakaryocyte/erythrocyte progenitors (MEP). CMPs give rise to all myeloid lineages whereas GMPs and MEPs give rise to cells in the granulocyte/monocyte and megakaryocyte/erythrocyte lineages respectively. The restricted differentiation capacity and lineage commitment of these cells have been clearly demonstrated by both in vitro culture and in vivo transplantation assay by Akashi et al. (2000) Nature 404, 193-197; and Na Nakorn et al. (2002) J. Clin. Invest. 109, 1579-1585. Whether monopotent progenitors for each myeloid lineage exist in the same manner is yet to be proven since they have not been prospectively isolated and tested for the in vitro and in vivo differentiation potentials at the clonal level.

In the megakaryocytic lineage, it is widely believed that CFU-MK are derived from monopotent megakaryocyte-committed progenitors (MKP) in the bone marrow. See, for example, Burstein et al. (1979) Blood 54, 169-179; Long et al. (1982) J. Cell. Physiol. 112, 339-344; Long et al. (1984) J. Clin. Invest. 74, 1686-1692; and Paulus et al. (1982) Proc. Natl. Acad. Sci. USA 79, 4410-4414.

The use of lineage committed progenitor cells circumvents many of the problems that would arise from the transfer of mature cells, and provides a means of screening for agents with highly specific activity. However, such progenitor cells must be separated from other hematopoietic cells. Separation requires identification of the cell and characterization of phenotypic differences that can be utilized in a separation procedure. Cells that are amenable to genetic manipulation are particularly desirable.

Relevant Literature

A number of review articles have been published addressing the phenotype of cells in hematopoietic lineages. Overall development of the hematolymphoid system is discussed in Orkin (1996) Curr. Opin. Genet. Dev. 6:597-602. The role of transcriptional factors in the regulation of hematopoietic differentiation is discussed in Georgopoulos et al. (1997) Annu. Rev. Immunol. 15:155-176; and Singh (1996) Curr. Opin. Immunol. 8:160-165. The phenotype of hematopoietic stem cells is discussed in Morrison & Weissman (1994) Immunity 1, 661-673; Spangrude et al. (1988) Science 241, 58-62; Enver et al. (1998) Blood 92, 348-351; discussion 352; Uchida et al. (1994) Blood 83, 3758-3779; Morrison et al., The aging of hematopoietic stem cells. Nat Med 2, 1011-1016 (1996).

SUMMARY OF THE INVENTION

A substantially enriched mammalian hematopoietic cell population is provided, which is characterized as a progenitor cell committed to the megakaryocyte lineage, herein referred to as MKP cells. These cells give rise exclusively to megakaryocytes and platelets, as evidenced by their growth and differentiation in vitro and in vivo. In vivo, MKPs do not have spleen colony-forming activity nor contribute to long-term multilineage hematopoiesis but give rise to platelets for about 3 weeks. The MKP cells are useful in transplantation, for experimental evaluation, and as a source of lineage and cell specific products, including mRNA species useful in identifying genes specifically expressed in these cells, and as targets for the discovery of factors or molecules that can affect them.

Positive selection for expression of CD9, CD41 and CD34 is used to separate the committed megakaryocyte progenitor cells from less committed progenitors and from mature megakaryocytes. Optionally, the cell population may also be negatively selected for expression of a lineage panel; Thy-1 (CD90); and/or IL-7Rα.

DESCRIPTION OF THE SPECIFIC EMBODIMENTS

Figure 1:
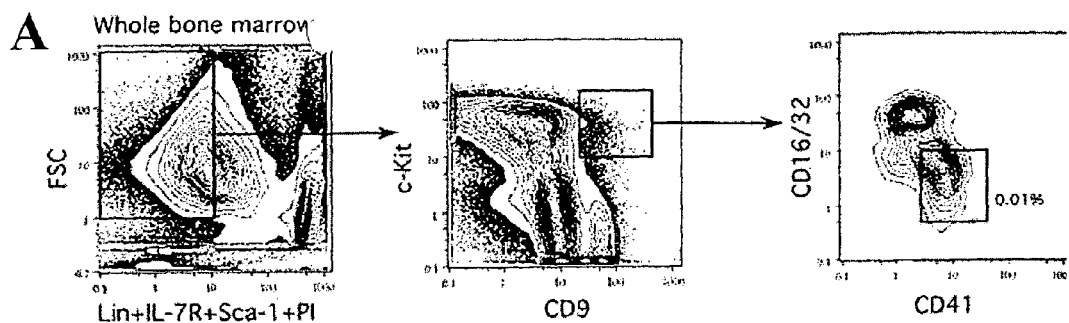
FIG. 1. Identification of MKPs in mouse bone marrow. A) Flow cytometric analysis of bone marrow after depleting the lineage-positive cells with magnetic beads. The sorting gates for MKPs are shown in the upper panel. The frequency of MKPs is shown as relative to total nucleated bone marrow cells before the negative depletion. Re-analysis after the first round of sorting found MKPs to be cleanly isolatable population (lower panel). B) MKPs were myeloblast-like cells with no characteristic features of megakaryocytes (Giemsa staining, original magnification×1000). C) DNA content analysis showed MKPs to be diploid cells. After a 5-day incubation with SCF and Tpo, polyploid (16N) megakaryocytes were found in the culture.
Figure 1:
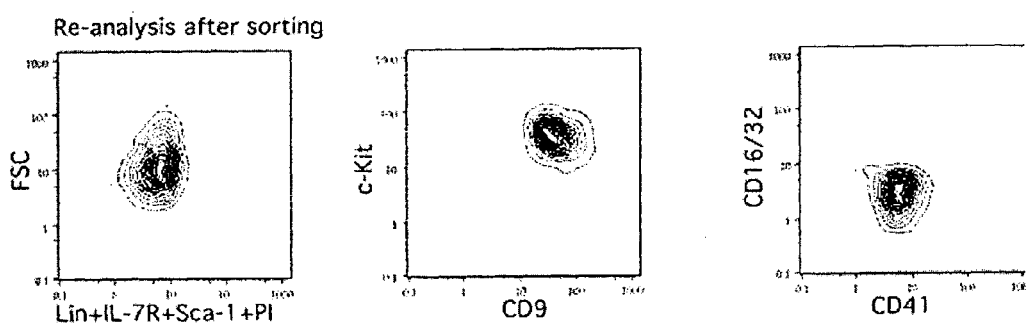
Figure 1:
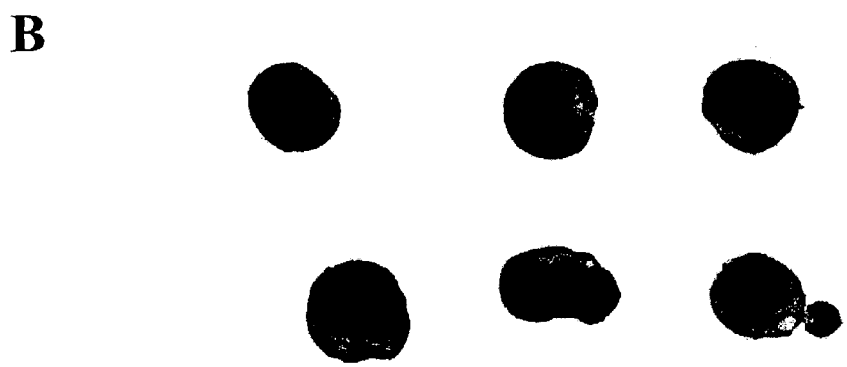
Figure 1:
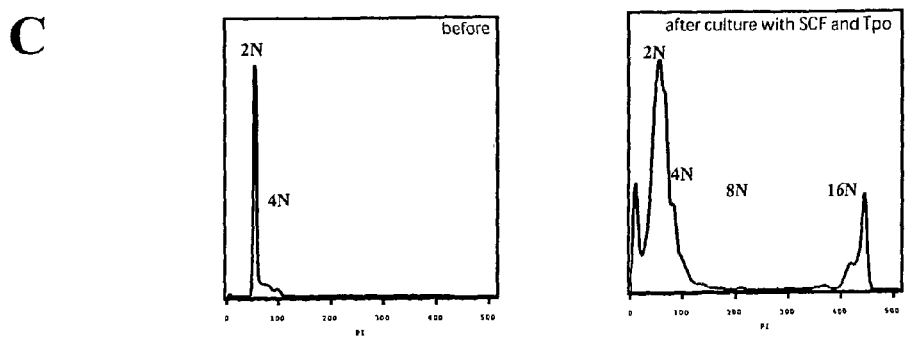

Mammalian hematopoietic progenitor cells committed to the megakaryocyte lineage are provided, herein termed megakaryocte progenitor, or MKP. The MKP population is useful in transplantation; for drug screening; experimental models of hematopoietic differentiation and interaction; screening in vitro assays to define growth and differentiation factors, and to characterize genes involved in megakaryocte development and regulation; and the like. The native cells may be used for these purposes, or they may be genetically modified to provide altered capabilities.

The megakaryocyte progenitor cells can be separated from a complex mixture of cells by using reagents that specifically recognize markers on the cell surface. The MKP cells express detectable levels of the markers CD41, CD9 and CD34. Optionally, the cells may be further selected for a lack of expression of the markers Thy-1 (CD90), IL-7Rα (CD127); and/or with a lineage panel of markers, as further described below. Other markers of interest include positive expression of CD38 and c-kit (CD117).

Platelets play an essential role in hemostasis and thrombosis. They are produced from bone marrow megakaryocytes and arise from fragmentation of the cytoplasm. If the level of circulating platelets drops below a certain number (thrombocytopenia), a patient runs the risk of catastrophic hemorrhage. Patients with cancer who have received chemotherapy or bone marrow transplants usually have thrombocytopenia, and the slow recovery of platelet count in these patients has been a concern. The demand for platelet units for transfusion has been steadily increasing primarily because of the need to maintain a certain platelet level in such patients with cancer or those undergoing major cardiac surgery. In addition to its use in patients with thrombocytopenia, agents that increase platelet counts may be considered for administration to normal donors of platelets.

Preclinical testing of full-length TPO or a truncated, pegylated derivative molecule has produced impressive results, with a dose-dependent increase in peripheral platelet count within 4 to 6 days after TPO administration. An issue, however, is the effectiveness of TPO administered after cytotoxic therapy since the drug can only be effective when the appropriate stem or progenitor cells are available for expansion and differentiation. The present invention provides a source of highly purified megakaryocyte progenitor cells, which are shown to give rise to platelets in vivo. The cells are also useful in testing agents such as growth and/or differentiation factors for stimulation of thrombogenesis.

Phenotypic Characterization

It will be understood by those of skill in the art that the stated expression levels reflect detectable amounts of the marker protein on the cell surface. A cell that is negative for staining (the level of binding of a marker specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but is not as intense as the most brightly staining cells normally found in the population. An alternative control may utilize a substrate having a defined density of marker on its surface, for example a fabricated bead or cell line, which provides the positive control for intensity.

Markers

The MKP cells are positive for CD34 expression. CD34 is a monomeric cell surface antigen with a molecular mass of approximately 110 kD that is selectively expressed on human hematopoietic progenitor cells. The gene is expressed by small vessel endothelial cells in addition to hematopoietic progenitor cells and is a single-chain 105-120 kDa heavily O-glycosylated transmembrane glycoprotein. The sequence is disclosed by Simmons et al. (1992) *J. Immun.* 148:267-271. Antibodies are commercially available, for example from BD Biosciences, Pharmingen, San Diego, Calif., catalog number 550760.

The MKP cells express the tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. CD9 interacts with the integrin family and other membrane proteins, and is postulated to participate in cell migration and adhesion. See, for example, Boucheix et al. (1991) *J. Biol. Chem.* 266:117-122. Antibodies are commercially available, for example from BD Biosciences, Pharmingen, San Diego, Calif., catalog number 559456.

The MKP cells express CD41, also referred to as the glycoprotein IIb/IIIa integrin, which is the platelet receptor for fibrinogen and several other extracellular matrix molecules. GP IIIa is a protein of 788 amino acids, including a 26-residue amino terminal signal peptide, a 29-residue transmembrane domain near the carboxy terminus, and 4 tandemly repeated cysteine-rich domains of 33-38 residues. Antibodies are commercially available, for example from BD Biosciences, Pharmingen, San Diego, Calif., catalog number 340929, 555466.

The MKP cells are positive for expression of CD117. CD117 recognizes the receptor tyrosine kinase c-Kit. This receptor has been particularly implicated with stem cells, including hematopoietic stem cells. Multiple isoforms of c-Kit also exist as a result of alternate mRNA splicing, proteolytic cleavage and the use of cryptic internal promoters in certain cell types. Structurally, c-Kit contains five immunoglobulin-like domains extracellularly and a catalytic domain divided into two regions by a 77 amino acid insert intracellularly; the sequence may be found in Yarden et al. (1987) *EMBO J.* 6 (11):3341-3351. Antibodies are commercially available, for example from BD Biosciences, Pharmingen, San Diego, Calif., Cat. No. 340529.

The MKP cells are positive for expression of CD38. CD38 is a 300-amino acid type II transmembrane protein with a short N-terminal cytoplasmic tail and 4 C-terminal extracellular N-glycosylation sites. The sequence is disclosed by Jackson et al. (1990) *J. Immun.* 144: 2811-2815. The marker is generally associated with lymphocytes, myeloblasts, and erythroblasts. Antibodies are commercially available, for example from BD Biosciences, Pharmingen, San Diego, Calif., catalog number 347680.

The MKP cells have the phenotype of lacking expression of lineage specific markers. For staining purposes a cocktail of binding reagents, herein designated "lin", may be used. The lin panel will comprise binding reagents, e.g. antibodies and functional binding fragments thereof, ligands, peptidomimetics, etc., that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells. Lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice.

The MKP cells are negative for expression of Thy-1 (CD90), which is a 25-35 kD molecule expressed on 1-4% of human fetal liver cells, cord blood cells, and bone marrow cells. Antibodies are commercially available, for example from BD Biosciences, Pharmingen, San Diego, Calif., catalog number 555595

Methods of Enrichment

Methods for enrichment of MKP cells are provided. The enriched cell population will usually have at least about 80% cells of the selected phenotype, more usually at least 90% cells and may be 95% of the cells, or more, of the selected phenotype. The subject cell populations are separated from other cells, e.g. hematopoietic cells, on the basis of specific markers, which are identified with affinity reagents, e.g. monoclonal antibodies.

Ex vivo and in vitro cell populations useful as a source of cells may include fresh or frozen cells, which may be fetal, neonatal, juvenile or adult, including bone marrow, spleen, liver, umbilical cord blood, peripheral blood, mobilized peripheral blood, yolk sac, etc. For autologous or allogeneic transplantation, bone marrow and mobilized peripheral blood are preferred starting materials. For peripheral blood, progenitor cells are mobilized from the marrow compartment into the peripheral bloodstream after treatment with chemotherapy; G-CSF or GM-CSF, or both. A number of single and combination chemotherapeutic agents have been used to mobilize cells. A review of peripheral blood stem cells may be found in Shpall et al. (1997) *Annu Rev Med* 48:241-251, and the characterization of stem cell mobilization in Moog et al. (1998) *Ann Hematol* 77(4):143-7. As an alternative source of cells, hematopoietic stem cells, as described in U.S. Pat. No. 5,061,620, issued on Oct. 29, 1991; and U.S. Pat. No. 5,087,570, issued Feb. 11, 1992, may be cultured and induced to differentiate in vivo or in vitro to provide a source of cells.

The progenitor cells may be obtained from any mammalian species, e.g. human, equine, bovine, porcine, canine, feline, rodent, e.g. mice, rats, hamster, primate, etc. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely.

The MKP cells are characterized by their expression of growth factor receptors. In addition to providing a convenient marker for separation, the cognate ligands find use in evaluating responsiveness to growth factors, and as ligands for separation. Growth factor receptors of interest expressed on MKP cells include c-kit (CD117). For example, the c-kit ligand, steel factor (Slf) may be used to identify cells expressing c-kit.

The subject cells are separated from a complex mixture of cells by techniques that enrich for cells having the above characteristics, preferably selecting for $CD34^+$, $CD41^+$, $CD9^+$ cells. Optionally the cells are further selected as $lin^-$, and may be further purified by selection for the phenotype $CD117^+$, $CD90^-$, $CD38^+$, $IL-7Ra^-$, and in the mouse, $Sca-1^-$.

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell populations will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g.

propidium iodide). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then separated as to the expression of cell surface markers as previously described, where an initial population may be limited to cells that are $CD34^+$, $CD41^+$, $CD9^+$. Optionally the cell population is further selected based on expression of a lineage panel; CD117, CD90, IL-7Rα, CCD38, and/or Sca-1.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for megakaryocyte progenitor activity are achieved in this manner. The subject population will be at or about 90% or more of the cell composition, and preferably be at or about 95% or more of the cell composition. The desired cells are identified by their surface phenotype, by the ability to respond to growth factors, and being able to provide for development in vivo and in vitro of megakaryocytes and platelets exclusively. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with hematopoietic cell proliferation and differentiation.

In Vitro Culture

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Of particular interest for the subject cells are factors that promote thrombopoiesis, including thrombopoietin. Specific growth factors that may be used in culturing the subject cells include steel factor (c-kit ligand), Flk-2 ligand, IL-11, IL-3, GM-CSF, erythropoietin and thrombopoietin. The specific culture conditions are chosen to achieve a particular purpose, i.e. differentiation into megakaryocytes, maintenance of progenitor cell activity, etc. In addition to the factors themselves, the activity of the factor may be provided through mimetics, antibodies that bind the cognate receptor, and the like. For example, a number of thrombopoietin mimetics are known in the art. Duffy et al. (2002) J Med Chem. 45(17):3576-8 identify a pharmacophore for thrombopoietic activity; and Cwirla et al. (1997) *Science* 276:1696 describe a mimetic of thrombopoietin that is highly active.

In addition to, or instead of growth factors, the subject cells may be grown in a co-culture with stromal or feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal cells (Small and Weissman [1996] *Scand J Immunol* 44:115-121).

The subject cultured cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

Megakaryocytopoiesis is likely to involve an interplay between stem and progenitor cells, stromal elements, and growth factors. There is a need to characterize these interactions, to define the factors that are involved, and to analyze the resulting production of platelets. The progenitor cells may be used in conjunction with the culture system in the isolation and evaluation of factors associated with the differentiation and maturation of megakaryocytes and platelets. Thus, the progenitor cells may be used in assays to determine the activity of media, such as conditioned media, evaluate fluids for growth factor activity, involvement with dedication of lineages, or the like.

Genes may be introduced into the MKP cells for a variety of purposes, e.g. replace genes having a loss of function mutation, markers, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are hematopoietic progenitor cells. For example, see Schwarzenberger et al. (1996) Blood 87:472-478; Nolta et al. (1996) P.N.A.S. 93:2414-2419; and Maze et al. (1996) P.N.A.S. 93:206-210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line. Lentiviral vectors such as those based on HIV or FIV gag sequences can be used to transfect non-dividing cells, such as the resting phase of human long term hematopoietic stem cells (see Uchida et al. (1998) P.N.A.S. 95(20):11939-44).

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895B2902) GRIP (Danos et al. (1988) *PNAS* 85:6460B6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the introduced gene after integration into a target cell genome. For some uses, however, it is desirable to have a regulatable promoter driving expression. Where such a promoter is included, the promoter function of the LTR will be inactivated. This is accomplished by a deletion of the U3 region in the 3'LTR, including the enhancer repeats and promoter, which is sufficient to inactivate the promoter function. After integration into a target cell genome, there is a rearrangement of the 5' and 3' LTR, resulting in a transcriptionally defective provirus, termed a "self-inactivating vector".

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types.

To prove that one has genetically modified progenitor cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the myeloid lineages while maintaining the ability to express the introduced DNA. Various tests in vitro and in vivo may be employed to ensure that the pluripotent capability of the cells has been maintained.

Transplantation

The subject MKP cells may be used for reconstitution of platelet function in a recipient, e.g. in thrombocytopenia. The condition may be caused by genetic or environmental conditions, e.g. chemotherapy, exposure to radiation, etc. Autologous cells, particularly if removed prior to cytoreductive or other therapy, or allogeneic cells, may be used for progenitor cell isolation and subsequent transplantation.

The progenitor cells may be administered in any physiologically acceptable medium, normally intravascularly, although they may also be introduced into bone or other convenient site, where the cells may find an appropriate site for regeneration and differentiation. Usually, at least $1\times10^5$ cells will be administered, preferably $1\times10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Screening Methods

The subject cells are useful for in vitro assays and screening to detect factors that are active on megakaryocyte progenitors, particularly those that are specific for megakaryocytic and lineages, and do not affect other lineages. Of particular interest are screening assays for agents that are active on human cells. A wide variety of assays may be used for this purpose, including immunoassays for protein binding; determination of cell growth, differentiation and functional activity; production of cytokines, e.g. IL-1; and the like.

Also of interest is the examination of gene expression in the MKP cells. The expressed set of genes may be compared between the progenitors and mature megakaryocytes, or against other hematopoietic subsets as known in the art. For example, one could compare the set of genes expressed in the MKP cells against stem cell or lymphoid progenitor cells.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of particular mRNAs in MEP cells is compared with the expression of the mRNAs in a reference sample, e.g. CMP cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed for the level of a polypeptide. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

EXAMPLE 1

Materials and Methods

Mouse strains. Six- to 8-week-old C57BI/Ka-Thy1.1 mice were used for the isolation of megakaryocyte progenitors (MKPs) and other myeloid progenitors. Competitive repopulation and spleen colony-forming unit (CFU-S) assays were done in the congenic Ly5 antigen system (Ly5.1 vs. Ly5.2) as described by Na Nakorn et al. (2002) *J. Clin. Invest.* 109: 1579-1585. β-actin green fluorescent protein (GFP) transgenic mice were generated in our laboratory (Wright et al. (2001) *Blood* 97, 2278-2285) and have been back-crossed to C57BI/Ka-Thy1.1 mice for at least 5 generations. All animals were maintained on acidified water (pH 2.5) in the Stanford University Laboratory Animal Facility in accordance with Stanford guidelines.

Cell staining and sorting. Myeloid progenitor cells (CMPs, MEPs and GMPs) were isolated using the staining protocol described previously by Akashi et al. (2000) *Nature* 404, 193-197. For the isolation of MKPs, bone marrow cells were stained with antibodies specific for the following lineage markers (Lin): CD3 (KT31.1), CD4 (GK1.5), CD8 (53-6.7), B220 (6B2), Gr-1 (8C5), Mac-1 (M1/70), TER119, Thy1.1 (19XE5) plus IL-7Rα (A7R34) and Sca-1 (E13-161-7). Lin$^+$ IL-7Rα$^+$Sca-1$^+$ cells were then removed with sheep anti-rat IgG-conjugated magnetic beads (Dynabeads M-450, Dynal A. S., Oslo, Norway), and the remaining cells were stained with Cy5-PE-conjugated goat anti-rat IgG polyclonal antibodies (Caltag Laboratories Inc., Burlingame, Calif.). After incubation with rat IgG (Sigma, St. Louis, Mo.), cells were stained with PE-conjugated anti-FcγRII/III (2.4G2), FITC-conjugated anti-CD41 (MWReg30; Pharmingen, San Diego, Calif.), biotinylated anti-CD9 (KMC8; Pharmingen) and APC-conjugated anti-c-Kit (2B8) monoclonal antibodies. CD9 was then visualized by Streptavidin-Texas Red (Caltag Laboratories Inc.).

Cells were sorted or analyzed using a highly modified triple laser (488-nm argon laser, 599-nm dye laser and UV laser) FACS Vantage (Becton Dickinson Immunocytometry Systems, Mountain View, Calif.). Progenitors were purified by two rounds of sorting to obtain the populations that were essentially pure for the indicated surface marker phenotype. In some assays, the resort was performed by using a carefully-calibrated automatic cell deposition unit (ACDU) system (Becton Dickinson). This system deposited a specific number of purified cells into each well of 24-well or 96-well plates.

DNA staining. Cells were fixed in ice-cold 80% ethanol for 30 minutes, washed twice with phosphate buffered saline (PBS) and then incubated overnight at 4° C. in 250 µl of propidium iodide (PI)/ribonuclease (RNase) solution (50 µg/ml of PI+10 µl/ml of RNase in 0.1% Triton X-100). The analysis was done on the FACScan cytometer (Becton Dickinson) using 488 nm excitation.

In vitro differentiation assays. The colony-forming assay was performed in methylcellulose medium (MethoCult M3231; StemCell Technologies, Vancouver, Canada) supplemented with SCF, IL-3, IL-11, Flt3-ligand, GM-CSF, erythropoietin (Epo) and thrombopoietin (Tpo) as described by Akashi et al., supra. Colonies were scored at day 10 of the culture using an inverted microscope. The morphology of cells in the individual colonies was confirmed by Giemsa staining. To evaluate the lineage relationships among the progenitors, 10,000 CMPs and MEPs were sorted onto OP9 stromal cell layers in 24-well plates with RPMI 1640 medium containing 10% fetal bovine serum (Summit Biotechnology, Fort Collins, Colo., USA) and cytokines (SCF, IL-11 and Tpo). Seventy-two hours later, cells were harvested and stained with monoclonal antibodies as described for the MKP isolation. They were later analyzed and sorted by FACS Vantage.

In vivo differentiation assays. The reconstitution assays were done by injecting 1,000 purified MKPs into the retro-orbital venous sinus of lethally-irradiated (9.5 Gy delivered in two fractions) Ly5-congenic recipients together with 200,000 host-type unfractionated bone marrow cells. CFU-S assays were performed with 500-1000 progenitor cells as previously described by Na Nakorn et al., supra. Spleens of the recipients were also subjected to standard histological examination. For the in vivo platelet readouts, progenitors were purified from β-actin GFP transgenic mice and transplanted into sublethally irradiated (4.5 Gy) C57BI/Ka. Mice were bled weekly after transplant for the flow cytometric analysis of GFP$^+$ platelets in the peripheral blood.

Results

MKPs reside within the CD9$^+$CD41$^+$FcγR$^{lo}$c-kit$^+$Sca-1$^-$IL-7Rα$^-$Thy1.1$^-$Lin$^-$ fraction of bone marrow. The expression of CD9 was first checked in the bone marrow cells of adult C57BI/Ka-Thy1.1 mice by flow cytometry. Virtually all Gr-1$^+$Mac-1$^+$ granulomonocytic (GM) and CD61$^+$ megakaryocytic cells expressed CD9 at high levels. In contrast, less than 5% of TER119+ erythroid cells were CD9+. Lymphoid cells moderately coexpressed CD9 with 15% positivity found in the B220+ B cells and 7% in the CD3+ T cells. In the c-kit+Sca-1−IL-7Rα−Lin− myeloid progenitor compartment, about 1-2% of cells were also found to be CD9+. They can be further subdivided into 2 populations according to the expression of CD16/32 (FcγR) and CD41 (shown in FIG. 1A). The CD41$^{lo}$FcγR$^{hi}$ fraction did not have significant myeloid colony-forming activity and was composed mainly of immature GM cells identified by Giemsa staining.

In contrast, CD41+FcγR$^{lo}$c-kit+Sca-1−IL-7Rα−Thy1.1−Lin− cells appeared to be all myeloblast-like cells (shown in FIG. 1B). Additional phenotypic analysis using antibodies to the other two markers for myeloid progenitors showed the uniformly positive expression pattern of both CD34 and CD38 in this population. These cells were clearly isolatable by FACS and represented ~0.008-0.012% of total nucleated bone marrow cells. They initially contained 2N-4N amount of DNA but developed into polyploid (16N) cells with the characteristic features of megakaryocytes when cultured with SCF and Tpo for 5 days (FIG. 1C). This population of cells will be hereafter referred to as MKP.

Figure 2:
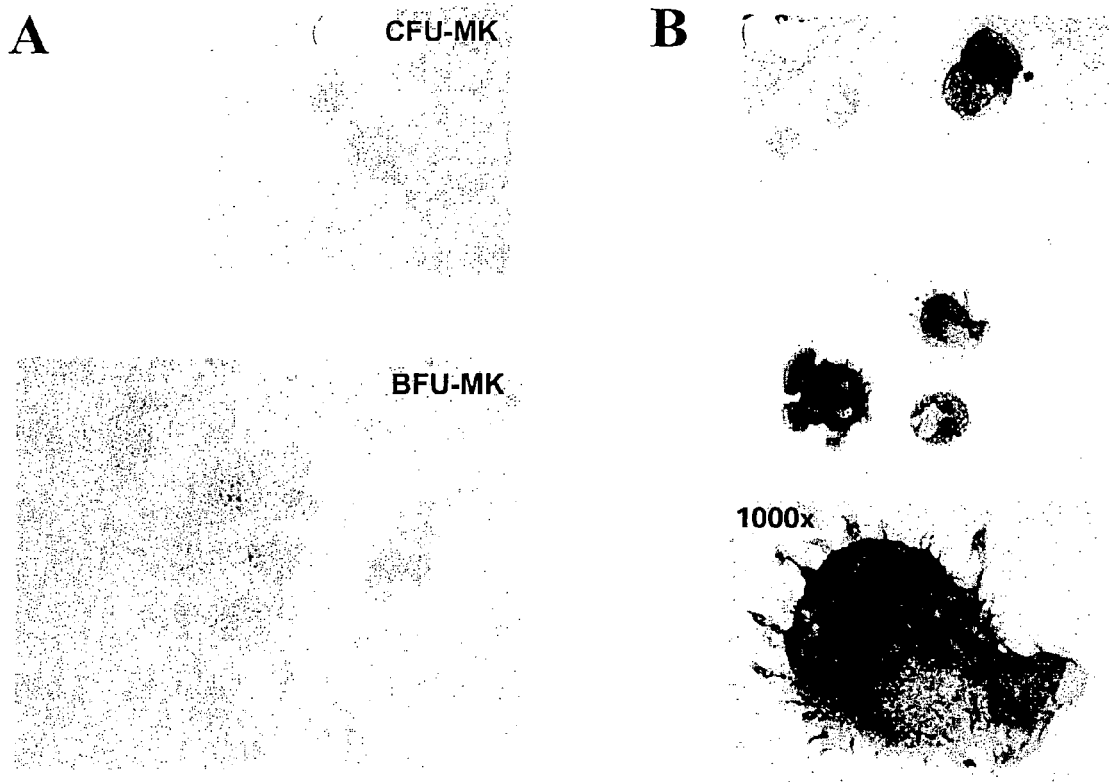
FIG. 2. Clonogenic megakaryocyte colony formation. A) Morphology of typical CFU-MK and BFU-MK derived from MKP at day 10 of culture (phase contrast; original magnification 100× for CFU-MK, 40× for BCU-MK). B) Mature megakaryocytes from a single colony (Giemsa; original magnification 200× and 1000×). C) Day-10 colony readouts of single progenitors in methycellulose containing SCF, Flt3-ligand, IL-3, IL-11, GM-CSF, Epo and Tpo. A total of 270 wells deposited with single progenitor were scored. CMPs gave rise to all types of myeloid colonies with plating efficiency greater than 80%. MEPs gave rise to both megakaryocyte and erythroid colonies while MKPs formed exclusively megakaryocyte colonies.
Figure 2:
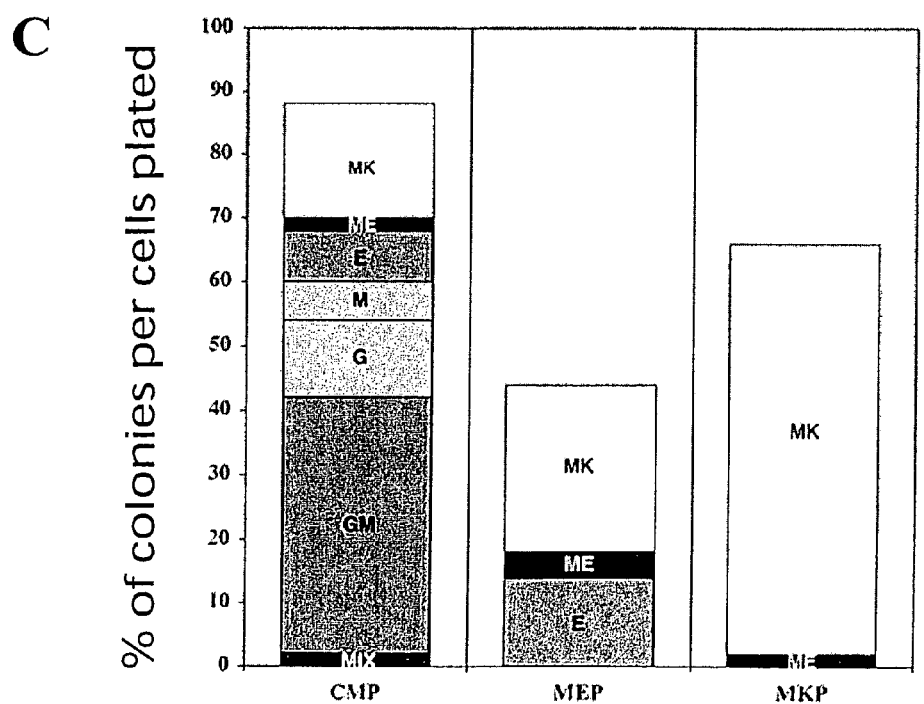

MKPs exclusively form megakaryocyte colonies in vitro. In the methycellulose culture system that was set up to detect all possible outcomes of myeloid differentiation, MKPs gave rise mainly to CFU-MK with less than 1% CFU-GM, CFU-M and BFU-E (Table 1). The readouts of these non-megakaryocyte colonies can be totally eliminated by using more restricted sorting gates, indicating that they were derived from the contaminants from the other progenitor pools rather than from MKPs. Interestingly, about 1-2% of MKP-derived colonies were large colonies that resembled the burst-forming unit-megakaryocyte (BFU-MK) previously described by Long et. al. (1985) *J. Clin. Invest.* 76, 431-438. The morphology of MKP-derived CFU-MK and BFU-MK are shown in FIG. 2A. Giemsa staining of cells in the individual colonies revealed that CFU-MK contained only mature megakaryocytes (FIG. 2B) whereas BFU-MK also frequently contained small numbers of erythroid cells. Therefore, these colonies should be more accurately defined as BFU-MK/E and probably represent the earlier stage of megakaryocyte progenitors.

TABLE 1

CFU activity of CD9+CD41+FcγR$^{lo}$c-kit+Sca-1−IL-7Rα−Thy1.1−Lin− cells.

| Experiment no. | CFU-MK | BFU-MK/E | BFU-E | CFU-GM | CFU-M |
| --- | --- | --- | --- | --- | --- |
| 1 | 47.6 ± 6.7 | 1.3 ± 0.6 | 0.3 ± 0.6 | 0 | 0 |
| 2 | 49.3 ± 11.0 | 1.3 ± 1.2 | 0.3 ± 0.6 | 1.0 ± 1.0 | 0 |
| 3 | 46.7 ± 7.2 | 1.3 ± 1.5 | 0 | 0 | 0.3 ± 0.6 |

One hundred cells were sorted directly onto 35-mm dishes containing methylcellulose medium supplemented with SCF, Flt3-ligand, IL-3, IL-11, GM-CSF, Tpo and Epo.
Colonies were counted at day 10.
CFU-MK were defined by the presence of three or more megakaryocytes and no other cell types in the colony. Each experiment was done in triplicate. The data are presented here as the average number of colonies per dish ± SEM.

To compare the clonogenic colony formation among the myeloid progenitor populations, single progenitors were sorted into each well of 96-well plate containing methylcellulose medium and cytokines. Ninety-nine out of 150 wells (66%) deposited with single MKP developed CFU-MK at day 10 of the culture (FIG. 2C). The average number of megakaryocytes in each colony was 3.9. In the same condition, 16.7% and 21.6% of CMPs and MEPs gave rise to CFU-MK with the average number of 8.9 and 8.7 megakaryocytes per colony, respectively. Large colonies including BFU-MK/E were more frequently derived from CMPs or MEPs than from MKPs. These results suggest that MKPs are committed only to the megakaryocytic lineage and are at least one step downstream of CMPs and MEPs in the developmental hierarchy of hematopoiesis. Thrombopoietin is required for CFU-MK activity of MKPs. We next tested the cytokine requirement for the development of megakaryocytes from MKPs.

TABLE 2

Effects of cytokines on the colony-forming activity of MKPs

| | Number of day 10 colonies/100 MKPs | | | |
| --- | --- | --- | --- | --- |
| Cytokines added | CFU-MK | BFU-MK/E | BFU-E | CFU-GM |
| SCF + IL-11 | 0 | 0 | 0 | 0 |
|  | 1 | 0 | 0 | 0 |
| SCF + IL-11 + Tpo | 28 | 0 | 0 | 0 |
|  | 31 | 0 | 0 | 0 |
| SCF + IL-11 + Epo | 3 | 0 | 1 | 0 |
|  | 2 | 0 | 0 | 0 |
| SCF + IL-11 + IL-3 + GM-CSF | 5 | 0 | 0 | 0 |
|  | 6 | 0 | 0 | 1 |
|  | 4 | 0 | 0 | 0 |
|  | 8 | 0 | 0 | 0 |
| SCF + IL-11 + Tpo + Epo | 29 | 0 | 0 | 0 |
|  | 34 | 0 | 0 | 0 |
|  | 42 | 0 | 1 | 0 |
|  | 37 | 0 | 0 | 0 |
| SCF + IL-11 + IL-3 + GM-CSF + Tpo + Epo | 61 | 0 | 1 | 1 |
|  | 46 | 2 | 0 | 0 |
|  | 55 | 1 | 0 | 0 |
|  | 42 | 3 | 0 | 0 |

As shown in Table 2, Tpo is the most important cytokine for CFU-MK formation. The plating efficiency of MKP dropped dramatically to less than 10% in the absence of Tpo. No colony was observed when MKPs were cultured with only early-acting cytokines such as SCF and IL-11. With the addition of Tpo alone, about 50-60% of the potential CFU-MK were rescued. Other cytokines had little, if any, effects on the CFU-MK development from MKPs. However, the synergy between GM-directed cytokines (GM-CSF and IL-3) and ME-directed cytokines (Epo and Tpo) was also observed. In fact, large CFU-MK including BFU-MK/E could be found only when all cytokines were present into the culture.

Figure 3:
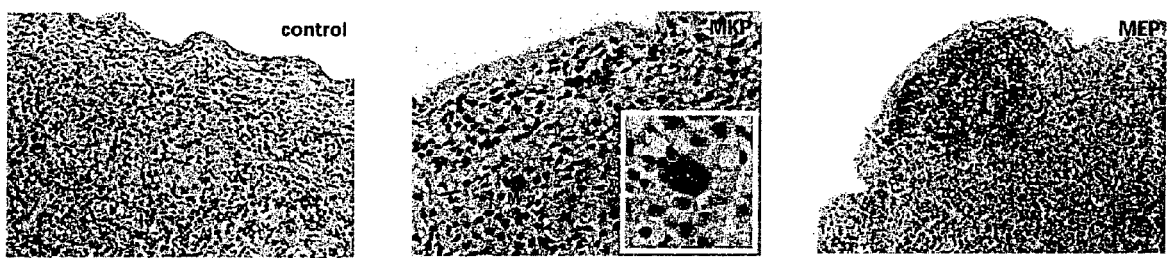
FIG. 3. In vivo differentiation of MKPs. A) Histology of the spleen at day 8 (Hematoxylin & Eosin, original magnification: control and MEP=200×, MKP=400× and inset=1000×). Mice were lethally irradiated then injected with no cell (control), 1000 MKPs or 500 MEPs. MKPs gave rise to microscopic foci of megakaryocytes (Meg) while MEPs formed large colonies comprised only of erythroid cells (E). No erythroid or megakaryocyte colonies were observed in the control animals. B) Representative FACS plots of platelets in the peripheral blood of recipient mice 14 days after receiving the purified progenitors from β-actin GFP transgenic donors. Blood cells were first gated on the forward scatter and side scatter. Percentages of $GFP^+CD61^+$ cells in the platelet gate are shown in the boxes. C) MKPs generated platelets in vivo for 3 weeks. The kinetics of platelet engraftment of 3000 MKPs was similar to 10,000 CMPs and MEPs (dashed lines). In contrast, 10,000 GMPs did not generate detectable platelets at any time point of analysis (black line). The threshold for detecting $GFP^+$ platelets in the whole population was 1 in 100,000.
Figure 3:
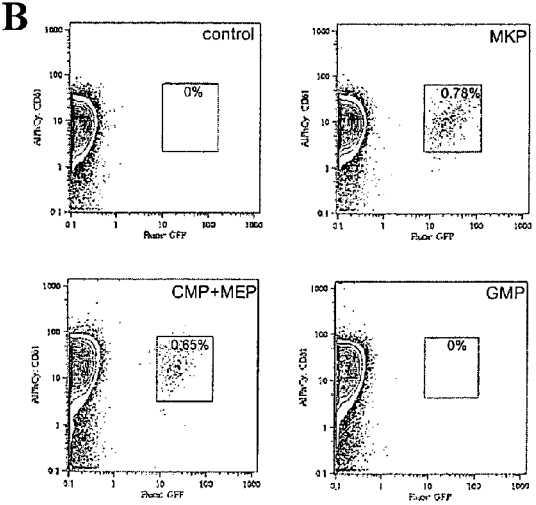
Figure 3:
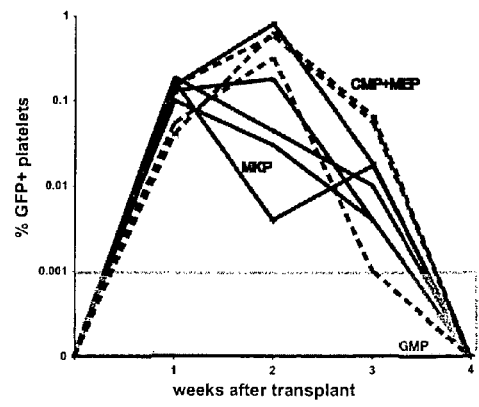

In vivo differentiation of MKPs. One thousand MKPs did not give rise to any surface colonies in the spleens of recipients at either day 8 or day 12. This was in contrast with the results of our previous experiments using the other myeloid progenitor populations in which we found MEPs to be the major source of day 8 CFU-S (14). However, histological examination of the day 8 spleens revealed some microscopic foci of megakaryocytes in mice receiving MKPs (FIG. 3A). At the same time point, CMPs and MEPs formed mainly erythroid colonies (FIG. 3A and Ref. 14), suggesting that MKPs are devoid of erythroid differentiation potential in vivo. In the reconstitution assays, no donor-derived Gr-1+, Mac-1+, CD3+, B220+ or Ter119+ cells were detected in blood, bone marrow or spleen of mice receiving 1,000 MKPs together with helper bone marrow cells. Since platelets do not express the Ly5 antigen, engraftment in the megakaryocytic lineage cannot be evaluated in this congenic system.

To measure platelet generation directly in vivo, we purified CD9+FcγR$^{lo}$c-kit+Sca-1−IL-7Rα− Lin−MKPs from the bone marrow of β-actin GFP mice and transplanted them into sublethally irradiated recipients. Similar to what was observed in the congenic transplant system, MKPs did not give rise to any GFP$^+$ GM, erythroid or lymphoid cells at any time point of analysis. However, they produced detectable levels of platelets in these mice (FIG. 3B). The peak of platelet engraftment occurred around day 14 after transplant, with the percentages of GFP$^+$ platelets in the peripheral blood ranging from 0.005 to 1%. No GFP$^+$ platelets were detected beyond three weeks after transplant (FIG. 3C).

In the same experiment, 10,000 CD9$^-$FcγR$^{lo}$c-kit$^+$Sca-1$^-$IL-7Rα$^-$Lin$^-$ cells (CMPs+MEPs) exhibited a similar pattern of platelet engraftment while 10,000 CD9$^-$FcγR$^{hi}$c-kit$^+$Sca-1$^-$IL-7Rα$^-$Lin$^-$ cells (GMPs) failed to generate any detectable platelets in the peripheral blood. This result confirms the previous observation that GMPs can only give rise to GM cells in vivo. More importantly, it excludes the possibility that GFP signals observed in the platelets may have been generated non-specifically from other transplanted GFP$^+$ cells. Taken together, these data demonstrate that MKPs do not have significant in vivo self-renewal capacity or multipotent differentiation potentials, but transiently give rise only to megakaryocytes and platelets.

Figure 4:
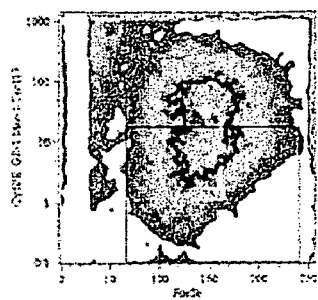
FIG. 4. Lineage relationships among myeloid progenitors. Flow cytometric analysis for cells with the MKP phenotype in the culture of CMPs and MEPs. Note more MKPs present in the CMP culture.
Figure 4:
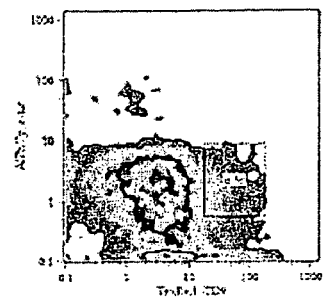
Figure 4:
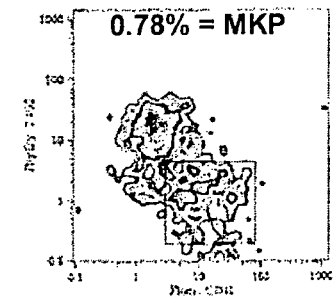
Figure 4:
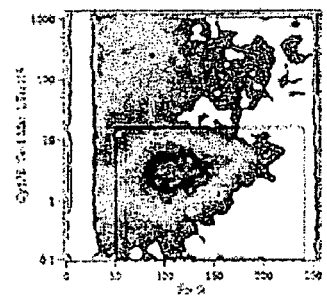
Figure 4:
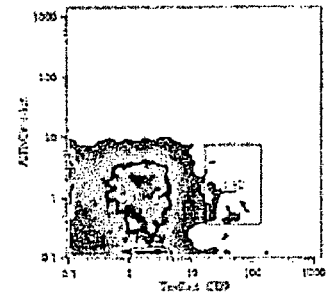
Figure 4:
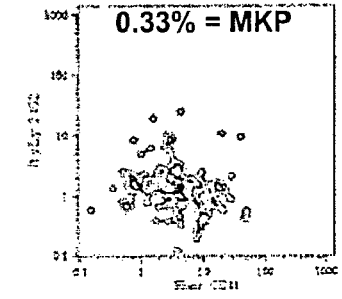

CMPs and MEPs gave rise to MKPs in vitro. To examine the relationships among the myeloid progenitors, we cultured CMPs and MEPs (CD9$^-$) on OP9 stromal layers in the presence of SCF, IL-11 and Tpo for 72 hours. Both CMPs and MEPs can give rise to cells with the phenotype of MKPs as found in freshly isolated bone marrow (FIG. 4A). These CD9$^+$CD41$^+$FcγR$^{lo}$c-kit$^+$Lin$^-$ cells represented ~0.78% and 0.33% of total cells in the CMP and MEP culture, respectively. They also formed only CFU-MK in methylcellulose culture. In the same culture condition, MKPs never gave rise to CMPs or MEPs but differentiated into multinucleated megakaryocytes within 5 days. These findings in combination with the results of single-progenitor colony formation assays demonstrates that MKPs are the committed progenitors downstream of CMPs and MEPs.

The concept of megakaryocyte-committed progenitors was introduced in the 1970's after the discovery of megakaryocyte colonies from the culture of mouse bone marrow cells in semisolid media. Since then several groups of investigators have developed culture systems to detect different types of megakaryocyte colonies in both humans and mice. Of those megakaryocyte-containing colonies described in the literature, large colonies that additionally contain cells in the other lineages are largely attributed to the multipotent progenitors, while pure megakaryocyte colonies are considered to represent the true monopotent megakaryocyte-committed progenitors. However, this assumption may not be entirely correct since many pure colonies were later found to be bi- or oligo-potent when the assays were done in different conditions. Moreover, in vivo experiments were rarely performed to confirm lineage restriction of these cells.

Recently, it has been reported that both MEPs and CMPs frequently give rise to CFU-MK and yet can also differentiate into cells of other lineages when injected into lethally irradiated mice. These findings raised the possibility that an isolatable precursor downstream of MEPs might be the origin of these megakaryocyte colonies. In this study, we prospectively searched for cells that could give rise to only megakaryocytes and extensively tested their differentiation potentials in several in vitro and in vivo assays. The MKPs isolated here meet all criteria for megakaryocyte-committed progenitors and therefore provide a definitive proof of the existence of these monopotent progenitors in mouse bone marrow.

Previous attempts to isolate megakaryocyte progenitors have included the use of various methods such as physical separation by sedimentation velocity, density gradient, cytochemical staining, in vivo enrichment with a chemotherapeutic agent 5-fluorouracil and, recently, flow cytometry, see, for example Pallavicini et al. (1987) *Exp. Hematol.* 15, 704-709; Bauman et al. (1987) *Exp. Hematol.* 15, 1074-1079; and Hodohara et al. (2000) *Blood* 95, 769-775.

Although the CFU-MK can be recovered in some isolated populations, a significant numbers of other CFU activities were always observed. One of the major limitations in the search for MKPs is the paucity of specific surface markers in the megakaryocytic lineage. In the human system, platelet glycoproteins (GP) such as GPIIb (CD41) or GPIIIa (CD61) have been widely used for the enrichment of megakaryocyte progenitors. Hodohara et al. has also shown recently that the CD41$^+$c-kit$^+$ bone marrow cells from Tpo-treated mice were highly enriched for CFU-MK activity. In the present culture system, these cells gave rise to significant numbers of CFU-GM and BFU-MK/E in addition to CFU-MK. Furthermore, it was found that the level of CD41 expression was not different among the three populations of myeloid progenitors. These observations are consistent with the studies in human and chicken, in which multipotent progenitors were reported to be CD41$^+$. Therefore, the CD41$^+$c$^-$kit$^+$ fraction of bone marrow contains other myeloid progenitor populations in addition to the MKPs.

CD9 belongs to the tetraspanin superfamily of cell surface proteins, which are generally involved in many cellular processes such as cell adhesion, motility, proliferation and differentiation as well as in signal transduction. CD9 is expressed in various tissues including bone marrow where the highest expression can be observed in platelets, megakaryocytes, granulomonocytic and stromal cells. Although the function of CD9 is still unknown, anti-CD9 antibody has been shown to inhibit myeloid differentiation of primitive progenitors in stromal cultures, presumably through the interaction with stromal cells, because it had no direct effect in the CFU assay. These present data indicate that CD9 is a useful differentiation marker to define the commitment into the megakaryocytic lineage.

Interestingly, CD9$^+$FcγR$^{hi}$c-kit$^+$Sca-1$^-$IL-7Rα$^-$Lin$^-$ cells do not have significant colony-forming activity in spite of the high expression of CD9 in GM cells. This result suggests that unlike in the megakaryocytic lineage, CD9 expression in the GM lineage occurs relatively late in development. This is confirmed by the fact that GMPs, the earliest GM-committed progenitors identified in bone marrow, only express CD9 at a low level and CD9 expression gradually increase along with the differentiation of GMP towards mature GM cells. Recently, mice lacking CD9 protein have been generated by two independent groups and are reported to have female infertility due to a defect in sperm-oocyte fusion. Surprisingly, no abnormality in the hematopoietic system was observed. The results from our data suggest that detailed analysis of the myeloid progenitors—particularly of the megakaryocytic lineage—should be done in these mice to address the role of CD9 in hematopoiesis.

The relationships of MKPs with the other two myeloid progenitors were also investigated in this study. The results of in vitro cultures clearly demonstrated that both CMPs and MEPs can give rise to MKPs. At the single cell level, they also generated larger CFU-MK with at least twice the numbers of megakaryocytes compared to the MKP-derived colonies. These results indicate that MKPs are indeed downstream of CMPs and MEPs.

In conclusion, clonogenic monopotent megakaryocyte-committed progenitors that uniformly generate CFU-MK in methylcellulose culture have been prospectively isolated.

They are downstream of CMPs and MEPs. MKPs do not show the properties of multipotent or oligopotent progenitors but are committed exclusively to the megakaryocytic lineage and give rise to platelets in vivo for only 3 weeks. As such, these cells find use ion the generation of platelets and megakaryocytes, and in the screening of agents that act in thrombopoiesis.

All publications mentioned herein are incorporated herein by reference for the purpose of describing and disclosing, for example, the compounds and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method of enrichment for a composition of mammalian megakaryocyte progenitor cells, the method comprising:
    combining reagents that specifically recognize CD41, CD9, CD34, CD2; CD3; CD4; CD7; CD8; CD10; CD11b; CD14; CD19; CD20; CD56; and glycophorin A with a sample; said sample selected from the group consisting of bone marrow and mobilized peripheral blood; and
    selecting for those cells that express CD41, CD, and CD34 and do not express CD2; CD3; CD4; CD7; CD8; CD10; CD11b; CD14; CD19; CD20; CD56; and glycophorin A,
    thereby providing a composition of mammalian megakaryocyte progenitor cells.

* * * * *

UNITED STATES PATENT AND TRADEMARK OFFICE
CERTIFICATE OF CORRECTION

| | | |
|---|---|---|
| PATENT NO. | : 7,494,807 B2 | Page 1 of 1 |
| APPLICATION NO. | : 10/661455 | |
| DATED | : February 24, 2009 | |
| INVENTOR(S) | : Nakorn et al. | |

It is certified that error appears in the above-identified patent and that said Letters Patent is hereby corrected as shown below:

In The Specification Under Column 1:

• Please replace lines 6-8 with:

-- This invention was made with Government support under contract CA042551 awarded by the National Institutes of Health. The Government has certain rights in this invention. --

Signed and Sealed this
Nineteenth Day of April, 2011

David J. Kappos
*Director of the United States Patent and Trademark Office*